United States Patent [19]
Meulenbrugge et al.

[11] Patent Number: 4,517,460
[45] Date of Patent: May 14, 1985

[54] METHOD OF CALIBRATING A GAMMA CAMERA, AND A GAMMA CAMERA INCLUDING A CALIBRATION DEVICE

[75] Inventors: Hendrik J. Meulenbrugge; Harm Fortuin, both of Eindhoven, Netherlands

[73] Assignee: U.S. Philips Corporation, New York, N.Y.

[21] Appl. No.: 389,637

[22] Filed: Jun. 18, 1982

[30] Foreign Application Priority Data

Jun. 24, 1981 [NL] Netherlands ............... 8103058

[51] Int. Cl.³ .................................. G01D 18/00
[52] U.S. Cl. ...................... 250/252.1; 378/207
[58] Field of Search ........... 250/252.1, 363 S, 363 R, 250/366, 369; 378/207

[56] References Cited

U.S. PATENT DOCUMENTS

| | | | |
|---|---|---|---|
| 3,515,878 | 6/1970 | Ried, Jr. et al. | 250/207 |
| 3,903,417 | 9/1975 | Peter | 250/369 |
| 4,179,607 | 12/1979 | Lange et al. | 250/363 S |
| 4,223,388 | 9/1980 | Nishikawa et al. | 364/521 |
| 4,228,515 | 10/1980 | Genna et al. | 364/571 |

Primary Examiner—Janice A. Howell
Assistant Examiner—Constantine Hannaher
Attorney, Agent, or Firm—Paul R. Miller

[57] ABSTRACT

A gamma camera is provided with a calibration device which samples the output signal of a photomultiplier tube/amplifier combination. After sampling, the calibration device determines a mean amplitude from the amplitudes of the samples with the mean amplitude being compared with a reference value, and the gain factor of the amplifier is corrected in order to eliminate a relative discrepancy occurring between the mean value and the reference value. To achieve this, the calibration device comprises a point source, a diaphragm with holes which are situated exactly in front of the centers of the photomultipliers, and a circuit which is controlled by a microprocessor for the sequential calibration of the amplifiers.

11 Claims, 5 Drawing Figures

METHOD OF CALIBRATING A GAMMA CAMERA, AND A GAMMA CAMERA INCLUDING A CALIBRATION DEVICE

The invention relates to a method of calibrating a gamma camera in which a point source is arranged in front of a scintillation crystal of the gamma camera in order to generate electrical signals by the scintillation crystal, photomultiplier tubes and amplifiers connected thereto, from which response-dependent signals are derived and employed to calibrate the photomultiplier tubes.

The invention also relates to a gamma camera which comprises a scintillation crystal, several photomultiplier tubes, each of which is connected to an amplifier, a calibration device with a point source for generating electrical signals, via the scintillation crystal, photomultiplier tubes and amplifiers, in order to derive therefrom response-dependent signals, and adjustment means for calibrating the gain of the photomultiplier tubes and/or amplifiers by means of the response-dependent signals.

A method of and a device for calibrating photomultiplier tubes in a gamma camera is known from European Patent Application Publication No. 0023.693. In the known device, a source which emits a thin collimated beam of gamma rays is arranged exactly in front of the center of a photomultiplier tube, after which the electric signals generated by all photomultiplier tubes are used to derive in known manner the Z signal which is a measure of the energy content of the gamma radiation intercepted by the scintillation crystal. The Z signal is compared with an upper and a lower reference signal. From the comparison values thus obtained, a response-dependent signal is derived which indicates whether the gain or the high voltage of the photomultiplier tube situated opposite the point source is too high, too low or correct. After readjustment of the gain if this is necessary, the point source is arranged opposite the next photomultiplier tube and the described procedure is repeated until the gains of all the photomultiplier tubes have been assessed and if necessary readjusted. Because the Z signal is derived from the electric signals of all the photomultiplier tubes, and to which the relevant photomultiplier tube under test makes a contribution of approximately 30%, is compared with the upper and the lower reference signal, no absolute certainty can be ensured that after adjusting the relevant photomultiplier tube/amplifier combinations under test, the gain of each combination will indeed have the same desired value. When the Z signal is determined, it is assumed that the gain of each photomultiplier tube/amplifier combination will be the same. This leads to an inexact determination of the Z signal, because the gain of each combination cannot in general be correct, and hence will lead to an inexact determination of the X- and Y-coordinate signals towards which the electric signal of each photomultiplier tube makes a contribution. A further consequence is that any corrections will tend to increase instead of reduce any inaccuracies because of non-linearities which are present.

The displacement of the reference point source (from a position centrally opposite a photomultiplier tube to a position centrally opposite the next photomultiplier tube) must be performed with adequate precision and it is experienced as being cumbersome.

It is an object of the invention to provide a method of calibrating a gamma camera, and a gamma camera with a calibration device by means of which an exact adjustment of the gain of each photomultiplier tube and/or associated amplifier can be achieved and in which the displacement of the gamma radiation source required for effecting the calibration, is no longer necessary.

To achieve this, a method for calibrating a gamma camera is characterized in that between the point source and the scintillation crystal there is arranged a diaphragm which is provided with domains which transmit gamma radiation, each domain being arranged in front of the center of a photomultiplier tube, after which the output signal of each photomultiplier tube is sampled and a mean amplitude of the samples of the output signal associated with the relevant photomultiplier tube is determined for each photomultiplier tube, after which the mean amplitude is compared with a reference value in order to provide a control signal for controlling the gain of the relevant photomultiplier tube and/or associated amplifier.

A gamma camera comprising a calibration device in accordance with the invention is characterized in that the calibration device furthermore comprises:

a diaphragm which is provided with radiation-transmitting domains, the mutual positions of which correspond to the mutual positions of the photomultiplier tubes, sampling circuit for sampling the output signals of the amplifiers, a memory device for storing the samples, and an arithmetic device for determining, from the stored samples which originate from a selected photomultiplier tube/amplifier combination, a mean amplitude which is associated with the relevant combination in order to compare the mean amplitude with a reference value in order to derive therefrom a response-dependent signal for the relevant combination in order to control the adjustment means for adjusting the gain of the photomultiplier tube and/or the amplifier of the relevant combination.

In accordance with the method, and in a gamma camera in accordance with the invention, the point source need not be displaced with respect to the photomultiplier tubes during calibration. Furthermore, the output signals of the photomultiplier tubes themselves are measured and compared with a reference value, so that the determination of a correction for the gain of a photomultiplier tube/amplifier combination will not be disturbed by the output signals of the other photomultiplier tubes.

An embodiment in accordance with the invention will be described in detail hereinafter with reference to the drawing; wherein.

Figure 1:
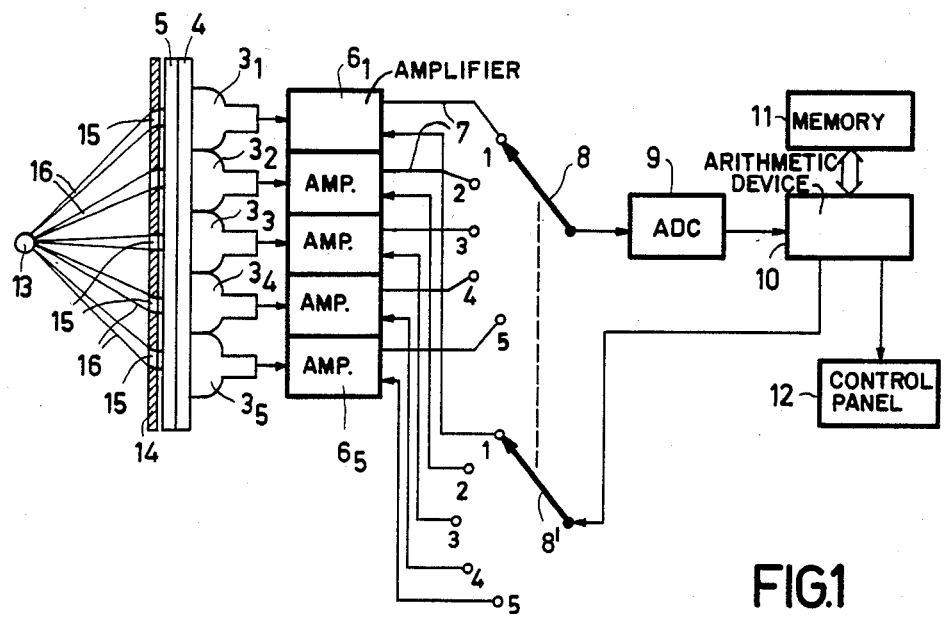
FIG. 1 shows diagrammatically a gamma camera with a calibration device in accordance with the invention.

FIG. 1 shows diagrammatically a gamma camera with a calibration device in accordance with the invention. The gamma camera comprises several photomultiplier tubes 3 which are arranged facing a light guide 4 and a scintillation crystal 5. The figure shows only five photomultiplier tubes $3_1 \ldots 3_i \ldots 3_5$. In practice, from 19 to 61 or even 91 tubes can be used in a hexagonal arrangement. Each photomultiplier tube $3_i$ is connected to an amplifier $6_i$ whose output 7 is connected in known manner (not shown for the sake of simplicity) to an impedance network in order to generate the X and Y coordinate signals and the Z signal which is a measure for the energy content of a detected gamma quantum. The outputs 7 of the amplifiers 6 are also connected to the calibration device, i.e. to switching means 8 which connect one of the amplifiers 6 to a sampling circuit 9. The sampling circuit 9 is connected to an arithmetic device 10 which stores the samples taken by the sampling circuit 9 in a memory 11. The arithmetic device 10 is actuated from a control panel 12. After the determination of a new amplifier setting by the arithmetic device 10 on the basis of the samples stored in the memory device 11, a control signal is applied to the relevant amplifier 6 by further switching means 8′. The control signal adjusts a gain factor for which purpose the amplifier 6 includes adjustment means which will be described hereinafter.

The calibration device also comprises a point source 13 and a diaphragm 14. The point surface 13 emits gamma radiation which is blocked by the diaphragm 14 with the exception of gamma radiation which is transmitted by domains or apertures 15 in the diaphragm 14. The diaphragm 14 is mounted in front of the gamma camera in the same manner as the collimator which is customarily used with a gamma camera but which should be removed when a calibration is to be performed. The diaphragm 14 may comprise a lead plate having a thickness of 3 mm, the radiation-transmitting apertures being between 3 to 12 mm across. The distance between the point source 13 and the diaphragm 14 is approximately 1 m; the position of the source 13 is not critical either in a direction perpendicular to the diaphragm 14 or in a direction transverse thereto. The "transmitted" radiation is denoted by beams 16 in the figure. The scintillations produced by the transmitted radiation are detected by the photomultipliers $3_i$. Only those output signals generated by radiation detected by the one photomultiplier $3_i$ are applied to the sampling circuit 9 by the amplifier 6 and the switching means 8. The sampled signals are stored in different registers of the memory device 11 in accordance with their amplitude value. In the registers, however, the amplitude values are not stored as such, but only as the frequency (number) with which a sampled signal (referred to hereinafter as sample) occurred within a given amplitude range. The memory device 11 in fact contains an amplitude spectrum of the sampled output signal of an amplifier 6.

Figure 2:
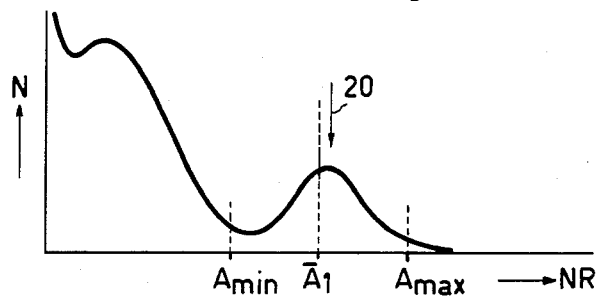
FIG. 2 shows diagrammatically a signal spectrum provided by a photomultiplier.

FIG. 2 shows such a spectrum. Along the horizontal axis are presented the identifying numbers NR of the registers in which the number of occurrences N (plotted along the vertical axis) are stored. The higher the number NR of a register, the greater will be the amplitude associated with the samples whose number of occurrences N is stored in the relevant register. Eventhough the spectrum is shown as a continuous line, it should be understood that the spectrum is represented by discrete steps. Both the register identification number NR and the occurrence numbers stored therein are positive integers. The gamma quanta passing through the opening 15 opposite the photomultiplier tube 3 after which the output signal is sampled, cause the peak in the spectrum which is denoted by an arrow 20. The scintillations caused by gamma quanta passing through the surrounding openings 15 but detected by the same photomultiplier tube, will be greater in number but will cause an output signal having a substantially lower amplitude, thus causing the "large" peak at the left in the spectrum. The position (register number NR) of the relevant peak (denoted by the arrow 20) will be determined by the radioisotope used as the point source. Thus, the relevant peak is a reliable measure for determining the actual gain of the combination formed by the photomultiplier 3 and the amplifier 6.

Figure 3:
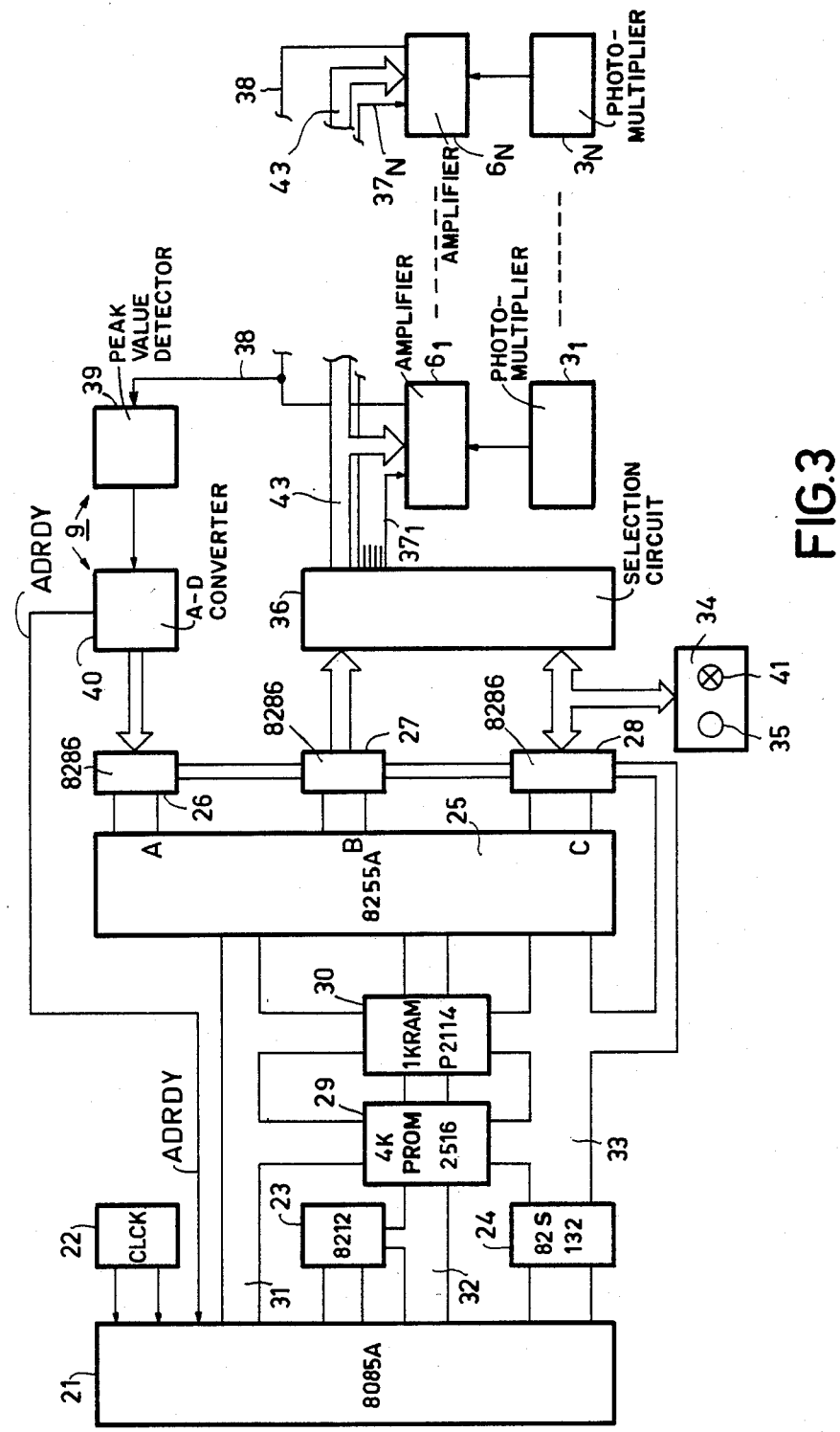
FIG. 3 shows a block diagram of the electrical circuitry of the calibration device.

FIG. 3 shows a block diagram of the electrical section notably the arithmetic device 10 and the memory 11 of the calibration device and a part of the gamma camera in accordance with the invention. The arithmetic device 10 shown in FIG. 1 comprises a microprocessor 21 (Intel 8085A), a clock pulse generator 22 (Intel 8224), an address memory buffer 23 (Intel 8212), an address decoder circuit 24 (Intel 82S132), an input and output gate control circuit 25 (Intel 8255A), and input and output gates 26, 27 and 28 (Intel 8286). The memory device 12 (FIG. 1) comprises a read-only memory 29 (ROM, INTEL 2516) and a random-access memory 30 (RAM, Intel P 2114). The microprocessor 21, memory (29,30), control circuits (24,25) and gates (26,27 and 28) are connected to respective data, address and control buses 31, 32, 33 in known manner.

Figure 5:
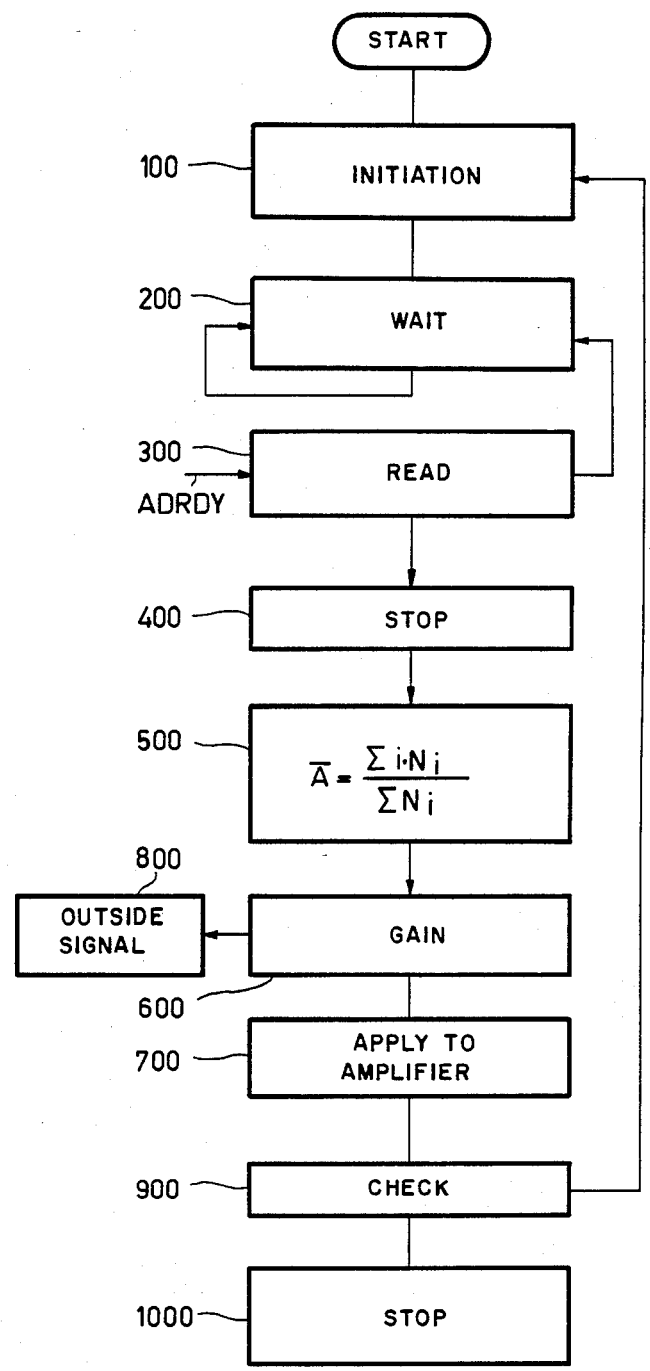
FIG. 5 shows a flow chart of a calibration procedure in accordance with the invention.

The calibration procedure is started by the input and output gate 28, by means of a start signal from a control panel 34 (start button 35) (see flow chart in FIG. 5). During a first step of the calibration procedure, the registers used for storing the amplitude spectrum, are cleared (see FIG. 2). Furthermore, a counter which counts the number of photomultiplier tubes which have already been calibrated, is reset to zero. A control signal which indicates that the gain of the first combination of photomultiplier tube $3_1$ and amplifier $6_1$ is to be calibrated, is presented to a selection circuit 36 by the control circuit 25 and the input and output gate 28. The digital control signal is decoded by the circuit 36. The selection circuit 36 supplies a selection signal by the output 37, so that the output of the amplifier $6_1$ is connected to the sampling circuit 9 via a connection 38. The sampling circuit 9 comprises a peak value detector 39 and an analog-to-digital converter 40. When the photomultiplier tube $3_1$ detects a gamma quantum, the peak value of the electrical pulse generated is retained by the detector 39. The analog-to-digital converter 40 converts the peak value into a digital number, after which it generates a signal ADRDY ("a/d converter ready") for the microprocessor 21 in order to store a sample in the memory 30 in which the spectrum registers are situated. The signal ADRDY is presented to an interrupt input of the processor 21 in order to interrupt a "wait" routine 200 in which the processor 21 operates after the initiation step 100 (see FIG. 5). The digital value generated by the converter 49 is read by the processor 21 (step 300, FIG. 5) and is donsidered as an address of a register in the memory 30. The contents of the relevant register is therefore incremented by the value "1". Subsequently, a test is carried out to determine whether the register is "full", i.e. to determine whether a desired number of samples with a given amplitude (step 300, FIG. 5) have been measured. As soon as one of the registers of the memory 30 is full, no further samples are input by the processor 21 (step 400). If the register is not full, the processor 21 returns to the wait routine (step 200, FIG. 5) until the analog-to-digital converter 40 supplies a next ADRDY signal, after which the step 300 is repeated.

When one of the registers of the memory 30 has been filled in the described manner, no further samples are input (step 400) and a mean amplitude $\overline{A}$ of the samples stored is determined (step 500, FIG. 5). The mean amplitude $\overline{A}$ is calculated according to the formula:

$$\overline{A} = \sum_i i \cdot N_i / \sum_i N_i$$

In the formula, the letter i is the address NR of a register i and $N_i$ is the number of samples stored in the register i. As will be apparent from FIG. 2, the number of samples relating to the amplitude of the relevant peak (see FIG. 2, arrow 20) will mainly determine the mean amplitude $\overline{A}$. The number $N_i$ of samples having a small amplitude is large, but because the amplitude of each of the samples is small, the mean value will not be seriously affected thereby. After calculation of a first mean amplitude $\overline{A}_1$, a further, similar, calculation can be performed (for example, by using further samples collected subsequently, in order to compensate for errors due to the statistical nature of the detection of gamma radiation). For performing the corresponding calculations, only the contents of those registers which correspond to amplitudes lying within a given limited amplitude range which is symmetrical with respect to the (provisional) mean amplitude $\overline{A}_1$, are employed. This is illustrated diagrammatically in FIG. 2. The mean amplitude $\overline{A}_1$ is plotted on the horizontal axis and the amplitude range is situated between the indices $A_{min}$ and $A_{max}$.

When a mean amplitude $\overline{A}$ has been determined, it is compared with a reference value associated with the photomultiplier tube $3_1$ by means of which the scintillations have been detected. From the equation there is obtained a relative discrepancy (error) value which is used to determine, in conjunction with the actual gain factor of the associated amplifier $6_1$ stored in the memory 30, a new setting thereof (step 600, FIG. 5). The new gain setting is applied to the amplifier $6_1$ by the control circuit 25, the output gates 27,28 and the selection circuit 36, and by the bus 43 (step 700, FIG. 5). Should the correction be such that the gain setting would be situated outside the maximum permissible gain control range of the amplifier $6_1$, an indication is given on the control panel 34 by means of an audio or light signal 41 (step 800, FIG. 5).

After the process of adjustment of the relevant amplifier to a new gain setting, the contents of the counter which counts the number of photomultiplier tube amplifier combinations ($3_i;6_i$ which have already been calibrated, is checked (step 900, FIG. 5). For as long as any combination remains uncalibrated, the counter contents are incremented by "1" and the calibration procedure for the next combination is started (step 100, etc.). When all the photomultiplier tube/amplifier combinations have been calibrated, the procedure is stopped (step 1000, FIG. 5).

Figure 4:
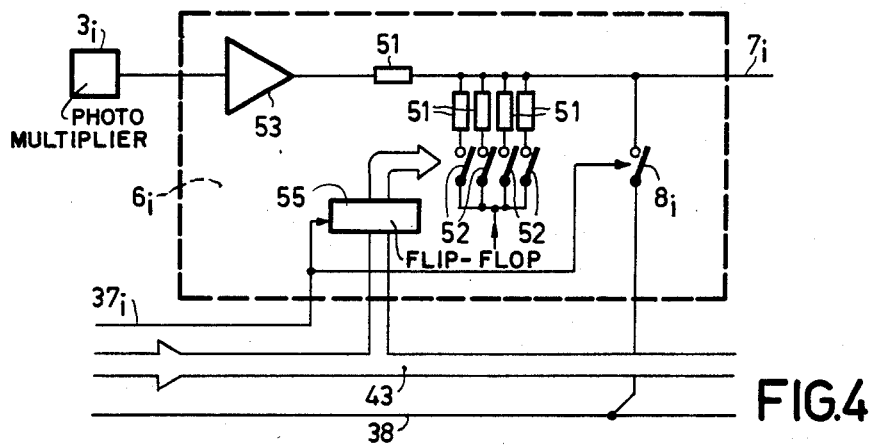
FIG. 4 is a circuit detail relating to the control of an amplifier connected to a photomultiplier.

FIG. 4 is a detailed representation of an amplifier $6_i$ which is connected to a photomultiplier tube $3_i$ and which comprises adjustment means for adjusting the gain. The adjustment means comprise switching means 52 (for example, switching transistors) and resistors 51 whereby the gain of a circuit 53 can be adjusted in known manner. The switching means 52 are controlled by the outputs of a latch flip-flop 55. Using a pulse on the control line $37_i$ (originating from the selection circuit 36), the content of the flip-flop 55 is made to correspond to the value applied via the bus 43. The pulse on the line $37_i$ is also used to operate the switch $8_i$ (a switching transistor) which connects an output $7_i$ of the amplifier $6_i$ to the connection line 38 (to the sampling circuit 9, FIG. 3).

What is claimed is:

1. A method of calibrating a gamma camera comprising the steps of positioning a point source in front of a scintillation crystal of the scintillation camera, arranging a plurality of photomultiplier tubes behind said scintillation crystal, connecting amplifiers to said photomultiplier tubes, and generating controls signals for calibrating said photomultiplier tubes and said amplifiers, characterized in that the following steps are carried out arranging a diaphragm between said point source and said scintillation crystal, said diaphragm being provided with radiation transmitting domains, said domains being arranged in front of centers of said photomultiplier tubes, sampling output signals of said photomultiplier tubes, determining a mean amplitude of said output signals associated with relevant photomultiplier tubes for each photomultiplier tube, and comparing said mean amplitude with a reference value to provide said control signals for controlling gains of at least one of said relevant photomultiplier tubes and associated amplifiers.

2. A method according to claim 1, wherein said diaphragm is arranged as close as possbile and parallel to said scintillation crystal, and wherein said point source is positioned from said diaphragm at a distance of at least 10 times a center-to-center distance of two neighboring photomultiplier tubes.

3. A method according to claim 1, wherein for each of said photomultiplier tubes, a series of samples of said output signal is sequentially recorded, digitized and stored.

4. A method according to claim 3, wherein said samples are amplitude discriminated and are stored according to amplitude value, and wherein said step of sampling said output signals is terminated as soon as a predetermined number of samples is obtained in an amplitude range.

5. A method according to claim 4, wherein said mean amplitude is determined by a quotient of a sum of amplitudes lying within an amplitude window centrally disposed about the amplitude most frequently measured and the number of samples in said amplitude range.

6. A method according to claim 1, wherein said samples are amplitude discriminated and are stored according to amplitude value, and wherein said step of sampling said output signals is terminated as soon as a predetermined number of samples is obtained in an amplitude range.

7. A method according to claim 6, wherein said mean amplitude is determined by a quotient of a sum of amplitudes lying within an amplitude window centrally disposed about the amplitude most frequently measured and the number of samples in said amplitude range.

8. A gamma camera comprising a scintillation crystal, a plurality of photomultiplier tubes, amplifier means connected to each of said plurality of photomultiplier tubes, calibration means with a point source for generating electrical signals by said scintillation crystal, said photomultiplier tubes, and said amplifier means, said electrical signals forming response-dependent signals, and adjustment means for calibrating gain of at least one of said photomultiplier tubes and amplifier means by said response-dependent signals, characterized in that said calibration means further comprises diaphragm means having radiation-transmitting domains with mutual positions corresponding to mutual positions of said photomultiplier tubes, sampling circuit means for sampling output signals of said amplifier means, memory means for storing samples from said sampling circuit means, and arithmetic means for determining from said stored samples a mean amplitude associated with a given combination of photomultiplier tube and amplifier means in order to compare said mean amplitude with a reference value, said comparison deriving said response-dependent signal for said combination to adjust gain of said photomultiplier tube and amplifier of said combination.

9. A gamma camera according to claim 8, wherein said sampling circuit means is connected to an output of said amplifier means by switching means, said switching means being operated by selection circuit means.

10. A gamma camera according to claim 9, wherein said arithmetic means includes a programmed microcomputer, input and output gate control circuits connected thereto, and input and output gates, said microcomputer being connected to said memory means, said sampling circuit means being connected to an input gate, and said selection circuit means being connected to at least one output gate.

11. A gamma camera according to claim 10, wherein said memory means includes a plurality of amplitude registers, each of said amplitude registers having the same storage capacity for storing the number of samples with an amplitude situated within an amplitude window associated with said register.

* * * * *